(12) United States Patent
Lopez et al.

(10) Patent No.: US 6,660,532 B1
(45) Date of Patent: Dec. 9, 2003

(54) MODULAR ASSEMBLY FOR REAGENTLESS AFFINITY SEPARATION AND DETECTION OF ANALYTE

(75) Inventors: Gabriel P. Lopez, Albuquerque, NM (US); Larry A. Sklar, Albuquerque, NM (US); Philip Hampton, Newbury Park, CA (US); Leonard Tender, Albuquerque, NM (US); Kimberly Opperman, Albuquerque, NM (US); Emmanuel Rabinovich, Albuquerque, NM (US); Ravinder K. Jain, Albuquerque, NM (US); Juchao Yan, Albuquerque, NM (US)

(73) Assignee: Science & Technology Corporation @ UNM, Albuquerque, NM (US)

( * ) Notice: Subject to any disclaimer, the term of this patent is extended or adjusted under 35 U.S.C. 154(b) by 0 days.

(21) Appl. No.: 09/402,682

(22) PCT Filed: Apr. 10, 1999

(86) PCT No.: PCT/US98/06871

§ 371 (c)(1),
(2), (4) Date: Dec. 16, 1999

(87) PCT Pub. No.: WO98/47001

PCT Pub. Date: Oct. 22, 1998

Related U.S. Application Data (60) Provisional application No. 60/043,501, filed on Apr. 11, 1997.

(51) Int. Cl.$^7$ .................... G01N 33/53; G01N 33/543
(52) U.S. Cl. .................... 436/518; 436/149; 436/164; 436/172; 436/501; 436/525; 436/527; 436/528; 436/537; 436/805; 436/806; 436/151; 436/165; 422/57; 422/68.1; 422/55; 422/82.01; 422/82.05; 422/82.08; 435/7.1; 435/7.8; 435/7.92; 435/287.1; 435/287.2; 435/288.7; 435/808; 204/193; 204/403

(58) Field of Search .................... 436/501, 164, 436/172, 518, 528, 805, 149, 151, 165, 525, 527, 537, 806; 422/68.1, 82.05, 82.08, 55, 57, 82.01; 435/7.1, 7.8, 7.92, 287.1, 287.2, 288.7, 808; 204/193, 403

(56) References Cited

U.S. PATENT DOCUMENTS

| | | | |
|---|---|---|---|
| 4,801,726 A | | 1/1989 | Giese et al. |
| 5,135,876 A | * | 8/1992 | Andrade et al. ............ 436/518 |
| 5,154,890 A | * | 10/1992 | Mauze et al. ............ 422/82.07 |
| 5,156,810 A | | 10/1992 | Ribi |

(List continued on next page.)

OTHER PUBLICATIONS

Tender et al Langmuir 1996 12 5515–5518.*
Pockrand et al. Nonradioactive decay of excited molecules near a metal surface. Chem. Phys. Lett. (1980) vol. 69, No. 3, pp. 499–504.*
K. Motesharei & D. Myles, "Molecular Recognition in Membrane Mimics. A Fluorescence Probe." J. Am Chem. Soc., vol. 116, 1994, pp. 7413–7414.
Tender, et al., *Electrochemical Patterning of Self–Assembled Monolayers onto Microscopic Arrays of Gold Electrodes Fabricated by Laser Ablation*, Oct. 15, 1996.

Primary Examiner—Long V. Le
Assistant Examiner—Kartic Padmanabhan
(74) Attorney, Agent, or Firm—Jagtiani + Guttag (57) ABSTRACT

The invention provides a reagentless assay kit for analyte in a sample comprising a modular affinity assembly including at least one sensor unit comprising a ligand having binding affinity for the analyte (affinity module) operatively associated with a reporter probe (reporter module) responsive to changes in the sensor unit induced by analyte/receptor complex formation by transduction of a characteristic detectable signal. Assays employing the modular assembly are also provided.

28 Claims, 5 Drawing Sheets

U.S. PATENT DOCUMENTS

| | | | |
|---|---|---|---|
| 5,156,972 A | * 10/1992 | Issachar | 435/288 |
| 5,229,302 A | 7/1993 | Miyazaki et al. | 436/537 |
| 5,268,305 A | * 12/1993 | Ribi et al. | 436/501 |
| 5,281,539 A | * 1/1994 | Schramm | 436/518 |
| 5,310,687 A | 5/1994 | Bard et al. | |
| 5,434,088 A | 7/1995 | Ikeda et al. | 436/525 |
| 5,491,097 A | * 2/1996 | Ribi et al. | 436/518 |
| 5,624,537 A | 4/1997 | Turner et al. | |
| 5,766,908 A | 6/1998 | Klein et al. | |
| 5,914,241 A | * 6/1999 | Valkirs | 435/17 |
| 5,942,388 A | * 8/1999 | Willner et al. | 204/193 |
| 5,972,692 A | * 10/1999 | Hashimoto et al. | 435/285.2 |

\* cited by examiner

B = BIOTIN
R = RHODAMINE
S = SUPPORT

MODULAR ASSEMBLY FOR REAGENTLESS AFFINITY SEPARATION AND DETECTION OF ANALYTE

CROSS-REFERENCE TO RELATED APPLICATIONS

This application makes reference to PCT Application No. PCT/US98/06871, entitled "Modular Assembly for Reagentless Affinity Separation and Detection of Analyte," filed on Apr. 10, 1998, and published in the English language on Oct. 22, 1998, which claims priority to U.S. Provisional Patent Application No. 60/043,501, entitled "Modular Assembly for Reagentless Affinity Separation and Detection of Analyte," filed Apr. 11, 1997. The entire disclosures and contents of the above applications are hereby incorporated by reference.

BACKGROUND OF THE INVENTION

The inventions described herein relate to the affinity separation and detection of analytes in a sample. In particular, they relate to reagentless binding assays which permit contemporaneous (real time) monitoring of analyte concentration, detection of analyte at very low concentrations, and which are easily generalized for detection and quantitation of a host of different analytes.

1. Field of Art

The assays of the invention employ unique modular affinity assemblies as affinity matrices for affinity separation, detection, and quantitation of analyte. The assembly includes at least one sensor unit, each comprising at least one anti-analyte receptor (affinity module) and at least one signal-competent reporter probe (reporter module) signal-responsive to events associated with analyte/receptor complex formation. While the sensor units are exemplified herein as optical sensor units comprising luminescent reporter probes (luminophors), the use of binding-sensitive reporter probes which transduce non-optical signals such as electron transfer signals such as electron transfer and radioactivity in the modular assemblies of the invention are also contemplated.

The inventions are particularly useful for the detection of very dilute concentrations of analyte (in the ng/ml-pg/ml range and lower), and for continuously reporting changing concentrations of analyte in "real time," (i.e., contemporaneously with the change in concentration), without further manipulation. Readings of the transduced signal can easily be taken at locations remote from the point of analysis, thus permitting, for example, constant monitoring of environmental air and water for pollutants, from afar.

Other applications for the assays of the invention include the clinical detection and real-time monitoring of trace biochemicals in body tissues and fluids, thus permitting, for example, the diagnosis and monitoring of biochemical markers of disease; the detection of trace amounts of hazardous (bio) chemicals in the environment such as those from medical, radioactive or industrial waste; the detection of pathogens (e.g., microorganisms and viruses or their toxins) in minute quantities in the atmosphere (including closed environments such as health-care facilities) or water supply; the detection of explosive materials; and the detection of proscribed substances such as controlled drugs.

2. Discussion of Related Art

Numerous assays based upon affinity chromatography are well-known for the detection of analyte in a sample. Typically, such assays involve immobilizing an analyte-specific, labelled ligand on a support to form an affinity matrix; contacting the immobilized ligand with a fluid sample potentially containing analyte; and detecting and/or quantitating bound analyte. Competitive binding assays, dependent upon competition between analyte and a labelled analyte analog for ligand binding sites are more complicated, additionally requiring labelled analyte analogs for initial saturation of matrix-bound ligands. Sandwich-type binding assays also additionally require labelled secondary ligands for sandwiching analyte bound to the primary immobilized ligand.

These classic assays have several drawbacks which make them unsuitable for achieving the objectives of the present invention. In both assays, the equilibrium eventually established between the analyte and immobilized ligand reflects a static sample analyte concentration, but fluctuations in the concentration cannot be detected without further addition of reagents, viz., labelled analog or labelled secondary ligand. Further, the assay is not reversible without time-consuming regeneration of the matrix, and even so this is not always possible. The present invention obviates the need for secondary labelling steps that require time for mixing, reaction, and flushing of excess reagent prior to detection and quantitation of analyte, and permits real-time continuous monitoring of analyte concentration without matrix regeneration.

The development of reagentless fluorescence-based sensors has long been a goal in this art. Several reagentless techniques that allow nearly real-time monitoring of chemicals have been developed, but all have been limited to a narrow range of analytes and receptors. In many of these techniques, the receptor itself is a fluorescent molecule (e.g., a metal ion chelator) whose fluorescent properties (e.g., emission intensity, emission wavelength, or lifetime) change upon analyte binding. Accordingly, a large effort has been expended on developing fluors that also have analyte recognition properties.

For example, a variety of cation-specific fluorescent dyes are commercially available that exhibit an intensity enhancement or a shift in their fluorescence emission spectra upon ion binding,. In addition to pH sensitive dyes, there are several known fluorescent probes that specifically chelate ions such as $Mg^{+2}$ (e.g., furaptra), $Zn^{+2}$ (TSQ), $Na^+$ (SBFI), $K^+$ (PBFI), and $Ca^{+2}$ (EGTA-AM) for use in the detection of relevant chemicals (Haugland, R. P., *Handbook of Fluorescent Probes and Research Chemicals*, Molecular Probes, 1996). These dyes have found wide application both in environmental sensing applications and in biochemical studies. The methods employed for detection of analyte with these dyes, however, have the disadvantage of requiring a specific receptor for the analyte that is also fluorescent, and whose fluorescent properties change upon analyte binding. Thus, they cannot be generalized to arbitrary analytes. Similar restrictions also apply to other optical sensor units used to detect excited state fluorophors or phosphors (Meier, B.; Werner, T.; Klimant, I.; Wolfbeis, O. S., "Novel Oxygen Sensor Material Based on a Ruthenium Bipyridyl Complex Encapsulated in Zeolite-Y: Dramatic Differences in the Efficiency of Luminescence Quenching by oxygen on Going, From Surface-Adsorbed to Zeolite-Encapsulated Fluorophores," *Sensors & actuators B* 2: 240, 1995).

A related reagentless approach is the use of environmentally-sensitive dyes with proteins, polymers, and in molecular assemblies (Lundgren, J. S.; Bright, F. V., "Biosensor for the Nonspecific Determination of Ionic Surfactants," *Anal. Chem.* 68: 3377, 1996). Dyes such as 6-propionyl-2-dimethylamino-naphthalene (prodan) and 6-dodecanoyl-2-dimethylamino-naphthalene (laurodan)

have been used for binding of a wide range of analytes. These dyes incorporate both electron donor and electron acceptor moieties that result in a large dipole moment in the excited state (Haugland, R. P., *Handbook of Fluorescent Probes and Research Chemicals*, Molecular Probes, 1996). Consequently, the emission spectra of these dyes are extremely sensitive to the polarity of their environment. For example, the emission maximum for prodan varies from about 380 nm when the dye is in a nonpolar environment (e.g., cyclohexane), to about 520 nm when the dye is in a polar environment (e.g., water) (Haugland, R. P., *Handbook of Fluorescent Probes and Research Chemicals*, Molecular Probes, 1996). In typical sensing protocols, these dyes are incorporated into polymers that swell in the presence of certain types of low molecular weight analytes (Barnard, S. M.; Walt, D. R. "A Fibre-Optic Chemical Sensor with Discrete Sensing Sites," *Nature* 353: 338–340, 1991). The degree of swelling of the polymer is directly proportional to the amount of analyte that has been imbibed by the polymer, and the resulting change in the polarity of the environment of the dye affects its fluorescence emission properties, which can then be correlated to analyte concentration. Similar techniques have been used to study the dynamics of cell membranes. For example, the effects of drugs, anesthetics, extracellular proteins, and metal ions on membrane dynamics and structure have been monitored by the incorporation of fluorescent probes such as diphenylhexatriene into the membrane structure (Haugland, R. P., *Handbook of Fluorescent Probes and Research Chemicals*, Molecular Probes, 1996). Although these general methods for fluorescence-based transduction allow reagentless monitoring of a variety of types of analytes, it is not broadly generalizable and it also lacks analyte specificity, as many background substances can cause changes in the environment of the fluorescent molecule that lead to confounding spectral data.

One type of reagentless, fluorescent sensor unit having a high degree of specificity comprises a specific binding receptor protein modified by covalent incorporation of reporter fluors. These sensor units are engineered so that emission properties of the fluor are changed with analyte/receptor binding. As an example, three general transduction mechanisms in which binding of analyte to the modified receptor results in a perturbation of the fluorescence emission have been identified (see Case et al and Sohanpal, K.; Watsuji, T.; Zhou, L. Q.; Cass, A. E. G., "Reagentless Fluorescence Sensors Based Upon Specific Binding Proteins," *Sensors & Actuators B* 11: 547, 1993). These are (1) perturbation of the fluor either through direct interaction with the analyte upon binding, or through indirect interaction via the receptor upon binding; (2) perturbation of the fluor caused by conformational changes in the receptor protein upon analyte binding that results in a change in the local chemical environment of the fluor; and (3) perturbation of the fluor caused by a change in the aggregation state of the receptor protein upon analyte binding. Although these transduction mechanisms are reagentless, reversible, and specific, they are too specific to be generalizable, as the fluor must be preattached to each protein receptor at a site that typically differs depending upon the protein receptor selected.

BRIEF DESCRIPTION OF THE DRAWING

In this Example, the molecular assembly is a self-assembled monolayer (SAM) formed by the reaction of $HS(CH_2)_{10}C(O)NH(CH_2)_2O)_2(CH_2)_2NHC(S)NH$—Rh wherein Rh=rhodamine, with the surface of a thin gold film. The cesium analyte binds to the oligo(ethylene glycol) moiety $NH(CH_2CH_2O)_2CH_2CH_2NH$ in the assembly, resulting in a change in the structure of the molecular assembly which reconforms the rhodamine to a less luminescent conformation.

In FIG. 3A, R represents a receptor module and L1 and L2 reporter modules. In one embodiment of the present invention, L1 and L2 may be excimer couples where binding of the analyte results in excimer emission. In another embodiment of the present invention L1 may be a luminophore and L2 is an effective quencher (through electron transfer or resonance energy transfer systems) and binding of the analyte results in decreased emission. Yet another embodiment of the present invention may include a reporter where L1 and L2 are capable of photoinduced charge transfer and binding of the analyte can result in either increased or decreased emission depending on the identity of L1 and L2.

SUMMARY OF THE DISCLOSURE

The invention provides a reagentless binding assay kit for analyte (ligate) in a sample comprising a sensor unit including a receptor or other ligand having binding affinity for the analyte (affinity module) operatively associated with a reporter probe (reporter module) responsive to changes in the sensor unit induced by analyte/receptor complex formation by transduction of a characteristic detectable signal.

In one embodiment, the invention provides a solid state, modular affinity matrix assembly including at least one such sensor unit immobilized on a solid affinity support. The modules of the assembly are physically constrained (ordered) by the assembly so that formation of bound analyte/receptor complexes disturbs the orderedness of the assembly and to cause physical, electrical and/or clinical changes directly or indirectly reportable by the reporter module. Luminescent reporters (luminophors) sensitive to changes in the orderedness of the modular assembly caused by the formation of receptor/antireceptor complexes are especially useful in assays requiring high sensitivity for bound analyte, as these reporters used in accordance with the invention are capable of detectably signalling the presence of as little as a single bound analyte.

The invention further provides assays employing the modular assembly of the invention.

DETAILED DESCRIPTION OF THE INVENTION

The modular assemblies of the present invention are affinity matrices including de minimis one sensor unit comprising a receptor (affinity module) and a reporter probe (reporter module) immobilized on an affinity support. The affinity module comprises any affinity ligand known in the art capable of forming a bound complex with a target analyte. For many applications, it will be desirable for the receptor to have a high specificity and affinity for the target analyte; however, receptors having broader affinities, such as those cross-reactive with related bacterial species, may be desirable for other applications. Contemplated analytes are myriad, and require only a complementary ligand to be a suitable target for assay according to the invention. Particular analytes include macromolecules such as proteins, whole cells, immunogenic peptides, and heavy metals.

The reporter module comprises any known signal-competent moiety capable of transducing a detectable characteristic signal in response to stereochemical events accompanying formation of bound receptor/analyte complex. These events include reporter perturbation upon binding of analyte caused by direct or indirect interaction with the analyte; conformational changes in the receptor; changes in the aggregation state of the receptor; changes in the chemical or dielectrical environment of the reporter module; and displacement of the reporter module relative to an effector module incorporated in the assembly. As noted above, particularly preferred reporter modules comprise optical reporters including luminophors and chromophors. These modules have emission properties modulatable in response to analyte/receptor complex formation, such as intensity, color, and lifetime of radiation; wavelength distance and frequency, shifts in spectra, and changes in polarization. Complex formation is readily detected and quantitated by a change in such emission properties by known techniques. Other reporters comprise enzyme- or redox-based electron transfer systems known in the art for their ability to transport detectable signals.

The reporter modules typically respond to complex formation by a fluctuation in signal; however, the modules may also have an on/off switch, responding by turning on a previously undetectable signal, or by turning off a detectable signal.

Effector modules are optionally incorporated into the modular assemblies for mediation of the signal response of the reporter module to affinity complex formation. Exemplary effector modules comprise, for example, excimer couples, collisional quenchers and resonance energy transfer donors or acceptors which are directly affected by receptor/analyte complex formation and in turn effect corresponding signal changes in luminophor or other reporters. Other effector modules include components such as metallic particles or films having dielectric properties which change the luminescent properties of luminophor reporters upon displacement of the luminophors relative to the dielectric material upon complex formation.

Thus, the detectable signal response may be 1) signal initiation and transduction (preparation), 2) signal extinction, or 3) signal fluctuation.

The module components of the assembly are disposed on the affinity support in operative relationship so that physical, electrical, or chemical events accompanying complex formation are transmitted to the reporter module, either directly or via an effector module, and result in a detectable signal of complex formation. The affinity module, while associated with the other modules of the invention within the assembly, is either affixed to the support so it is spaced from the reporter module, or the reporter and affinity modules are linked. Each of the sensor units of the assembly comprises at least one receptor and one reporter module immobilized on the support; the modules may be the same or different. The receptor module may differ from unit to unit, but be associated with the same reporter module, and vice versa; each unit may have the same reporters and receptors; or both reporter modules and receptor modules may differ from unit to unit. For example, a first sensor unit may include an antibody to virus A as receptor with an associated fluor reporter, while a second sensor unit may include an antibody to virus B as receptor with an associated phosphor reporter. Such a modular assembly is particularly suitable for sampling an environment for a variety of possible analytes by inducing different signals for different bound analytes. The received signals may then be read and quantitated for specific analyte. Possible subunit constructs include:

SU = sensor unit
A, A' = affinity modules
B, B' = reporter modules

The support comprises a solid, optionally rigid, substrate selected from materials known in the art for affinity ligand immobilization. Criteria for such supports are known; for example, the support should be free from extraneous ion-exchange sites, should not promote non-specific binding, should be mechanically strong enough for the contemplated application, should be biologically and chemically inert, and be adapted for ligand immobilization. The support should also be stable under reaction conditions (e.g. for ligand immobilization) and in its intended environment for use. Useful supports for module immobilization according to the present invention comprise organic polymers, metals, semiconductors, and ceramics. The support may comprise a mixture of these materials, such as an organic polymer layer bonded to an inorganic layer to provide attachment sites for certain affinity modules, or a non-conducting oxide layer on a metallic or other substrate. For most applications, the affinity support will comprise a relatively thin film or composite film as further described infra.

Modular engineering of reagentless analyte sensor units according to the invention includes the manufacture of a minimum combination of two modules having the separate functions of (a) analyte binding affinity (affinity module) and (b) recognition-responsive signalling (reporter module). The sensor units are engineered into the assembly so that the binding event between the receptor and analyte affects the signalling properties of the reporter module sufficiently to permit detection of the event. The modular design concept is attractive because it is useful with a variety of receptors and their target analytes. Thus far, however, it has been only used to generate indicators for binding of heavy metal ions in solution.

Modular Assemblies. The modular assemblies of the invention are prepared by covalent or non-covalent attachment of component modules, to a solid affinity support or substrate such as a metal, semiconductor, ceramic or synthetic or natural organic polymer. They are solid-state assemblies. herein distinguished from other affinity matrices having affinity supports comprising fluid, free-standing membranes such as lipid bilayers, vesicles and Langmuir films. The solid state assemblies of the invention are engineered for sufficient structural stability so that direct or indirect perturbation of the reporter module to cause signal changes reliably reflects complex formation rather than extraneous events. The supports comprise known materials used in the art for the immobilization of affinity ligands. These materials include self-assembled monolayers (SAMs); polymeric brushes and grafted polymers. Materials that are ordered assemblies (e.g., SAMs of alkylthiols on noble metals and some semiconductors, of silanes on oxides, or of carboxylic acids on basic oxides, polymer brushes and certain grafted polymers, are herein distinguished from those that are normally relatively disordered such as polymer gels and surface-adsorbed insoluble polymers. There have been only a few reports on the use of such assemblies for reagentless chemical sensing (Motesharei, K.; Myles, D. C., "Molecular Recognition in Membrane Mimics: A Fluorescence Probe," *J. Am. Chem. Soc.* 116: 7413, 1994), and no reports of transduction mechanisms based on changes in the orderedness of modular assemblies upon analyte binding and detecting.

Luminescence-Based Sensor units. A number of virtues make measurement of changes in luminescence (e.g., fluorescence, phosphorescence) properties a desirable method of transduction in affinity-based sensor units. Under appropriate conditions, luminescence spectroscopy can be used to probe extremely low concentrations of analyte; changes in fluorescence spectra and lifetimes can even be detected from a single molecule (Ambrose, W. P.; Goodwin, P. M.; Martin, J. C.; Keller, R. A. "Alterations of Single Molecule Fluorescence Lifetimes in Near-Field Optical microscopy," *Science* 265: 364, 1994). Luminescence can essentially function as an amplification mechanism, as a single luminophor can be subjected to multiple cycles of excitation and emission, each of which reflects the binding state of a receptor with which the luminophor is associated. Other useful properties of luminescence include the fact that intensity of absorbance and emission at various wavelengths, luminescence polarization, and excited state lifetime, are all properties of the luminophor that are, in general, sensitive to the chemical and electrical environment of the luminophor. Hence, these properties can all be used to advantage in a multi-measurement analysis of the binding state of a receptor with which the luminophor is associated for real time monitoring of analyte. Recent advances in measurement of excited state lifetimes, for example, are particularly relevant to affinity complex sensing, as they have led to the development of compact instrumentation for measuring phosphorescence and fluorescence lifetimes in schemes that are relatively insensitive to external interferences such as spurious light sources and photobleaching effects (Meier, B.; Werner, T.; Klimant, I.; Wolfbeis, O. S., "Novel Oxygen Sensor Material Based on a Ruthenium Bipyridyl Complex Encapsulated in Zeolite-Y: Dramatic Differences in the Efficiency of Luminescence Quenching by Oxygen on Going, From Surface-Adsorbed to Zeolite-Encapsulated Fluorophores," *Sensors & actuators B* 29: 240, 1995).

As described above, the present inventions are based on modular assemblies that incorporate affinity and reporter modules selected and disposed on the support so that binding of an analyte to the receptor (affinity) module results in one or more changes in the architecture (order) of the molecular assembly to which the luminescent or other properties of the reporter module are sensitive. Examples of such changes are: (1) a change in the structure of the modular assembly resulting in a change in the average distance between the luminescent centers of a luminophor module and a solid substrate having appropriate dielectric properties (e.g., n and k) so that the original luminescent properties of the luminophor are changed upon analyte binding; (1) (b) a change in the structure of the assembly resulting in a change in the average distance between an electroactive reporter probe, e.g., a redox reporter such as viologen or a redox enzyme such as horseradish peroxide; (2) a change in the structure of the modular assembly so that the transport properties of quenchers such as oxygen are modified upon analyte binding; (3) a change of the structure of modular assemblies so that the luminescent properties of a luminophor reporter are indirectly affected by effector modules built into the modular assembly such as excimer couples, collisional quenchers and resonance energy transfer donors or acceptors; (4) a change of the structure of modular assemblies so that the luminescent properties of luminophor reporter modules such as fluors and phosphors are directly affected by the analyte, for example, through collisional quenching, photoinduced electron transfer, or resonance energy transfer. Several examples of covalently-linked receptor and transducer modules based on photoinduced electron transfer (PET) are known; (see, e.g., Prasanna de Silva, A.; Gunnlaugsson, T.; Rice, T. E., "Recent Evolution of Luminescent Photoinduced Electron Transfer Sensors," *Analyst* 121: 1759, 1996; Fabbrizzi, L.; Licchelli, M.; Pallavicini, P.; Sacchi, D.; Taglietti, A. "Sensing of Transition Metals Through Fluorescence Quenching or enhancement: A Review," *Analyst* 121: 1763, 1996, incorporated herein by reference). Such mechanisms permit the generalization of the present affinity matrices to permit the facile detection of a host of analytes.

A particularly significant aspect of the invention is the enablement of binary or higher order modularity of function provided by the inventive modular concept. In addition to the affinity (receptor) and reporter (e.g., luminophor) modules in the assemblies, modules performing additional functions may also be included. For example, for sensing in biological fluids an anti-fouling module comprising, for example, polyethylene glycol or a highly-hydrated polysaccharide can be included to eliminate biofouling of the affinity matrix.

EXAMPLES

Figure 1:
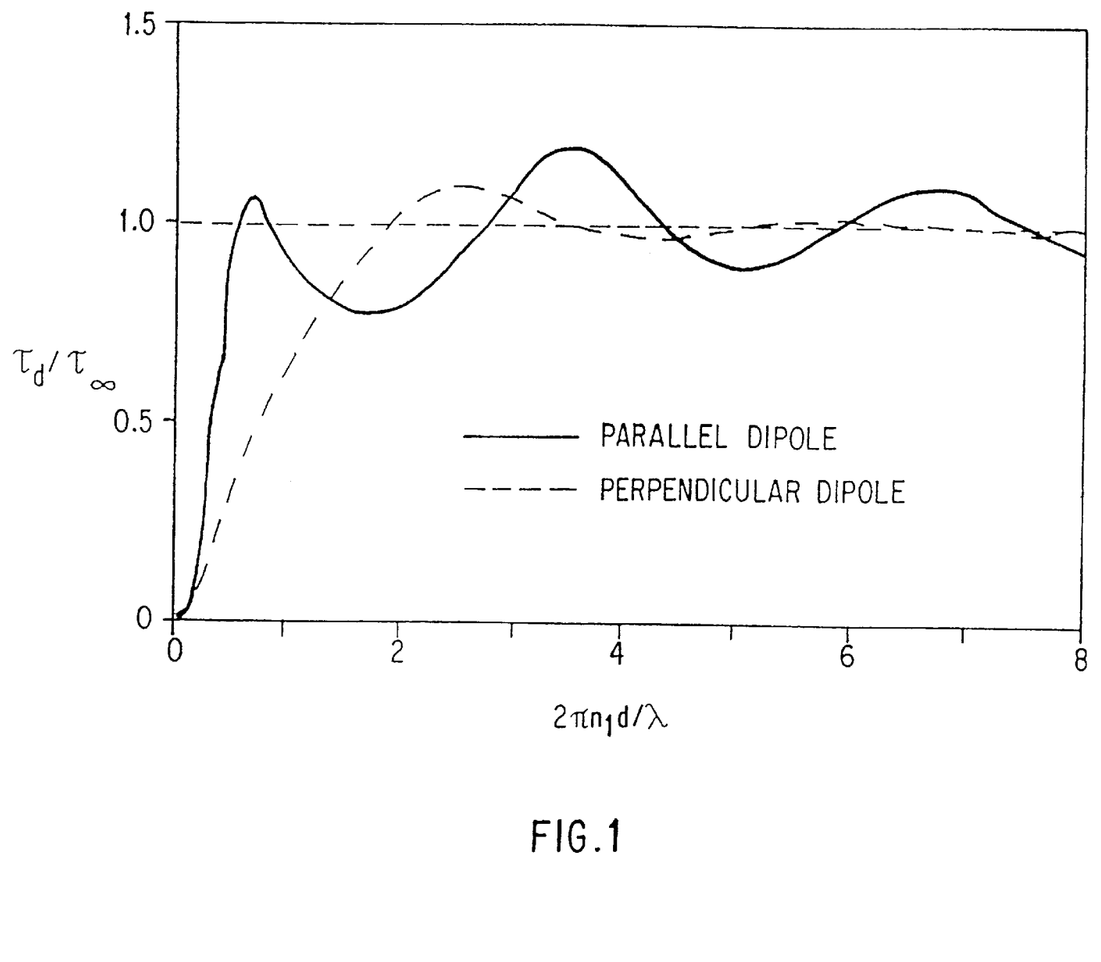
FIG. 1: Dependence of the relative fluorescence lifetime on distance of separation between a fluorophore and a metal surface, as estimated by Kuhn's approximation theory. (Figure is adapted from Chen, H. C.; Frank, C. W., "Fluorescence Probe Studies of Self-Assembled Monolayer Films," *Lancimuir* 7: 1791, 1991).

I. Transduction Through Change of the Distance Between Reporters and Their Support Upon Analyte Binding Within a distance approximately equivalent to the thickness of the modular assemblies envisioned here (typically about ~10 Å–1 µm), the radiative emission of fluorophors and phosphors is known to be very sensitive to their separation from metals and other materials (Pockrand, I.; Brillante, A.; Mobius, D., "Nonradiative Decay of Excited Molecules Near a Metal Surface," *Chemical Physics Letters* 69: 499–504, 1980). For example, FIG. 1 illustrates the dependence of fluorescence lifetime on distance of separation from a metallic surface, as estimated by Kuhn's approximation theory. For rhodamine ($\lambda$emission ~600 nm), and $n_1$=1.45 (the approximate value for close-packed hydrocarbon assemblies), a value of 1.0 on the X-axis corresponds to a separation distance of ~65 nm. This separation is in the midrange of thicknesses for the thin film molecular assemblies envisioned here.

To a first approximation, the components of the complex index of refraction (n and k) of the substrate can be used, together with the separation distance and the orientation of the fluor or phosphor relative to the substrate surface and the roughness of the substrate surface, to estimate how strongly the surface will influence the lifetime and emission intensity of the reporter (Chen, H. C.; Frank, C. W., "Fluorescence Probe Studies of Self-Assembled Monolayer Films," *Langmuir* 7: 1791, 1991). Several new types of synthetic molecular assemblies are described below that can take advantage of these phenomena in the transduction of binding of an analyte to a modular assembly. In the following Examples a synthetic (bio)organic assembly is formed either directly on a metallic surface (e.g., gold, silver), on an nonconducting oxide on a metallic surface or on any other solid support (e.g., semiconductor, oxide, organic polymer) that can function either as a spacer from the metallic surface or, if designed with the appropriate dielectric properties as known in the art, also as the module that perturbs the signalling properties of the reporter module. The following Examples demonstrate transduction by direct measurement of fluorescence lifetime, or by measurement of fluorescence intensity and/or polarization that may correlate with fluorescence lifetime. Very thin films of metals or other materials that are transparent to excitation and emitted light can be formed on supports for compact sensing platforms based, for example, on evanescent wave excitation.

In addition to luminescent reporters, other reporters sensitive to changes in their distance from a metallic or other support may be employed. These include redox reporters such as electroactive chemical and biochemical compounds, e.g., ferrocene, viologen, and enzymes that catalyze redox reactions.

Example I.

IA. Conformational Changes in the Receptor Near a Metallic or Other Influencing Substrate.

Figure 2:
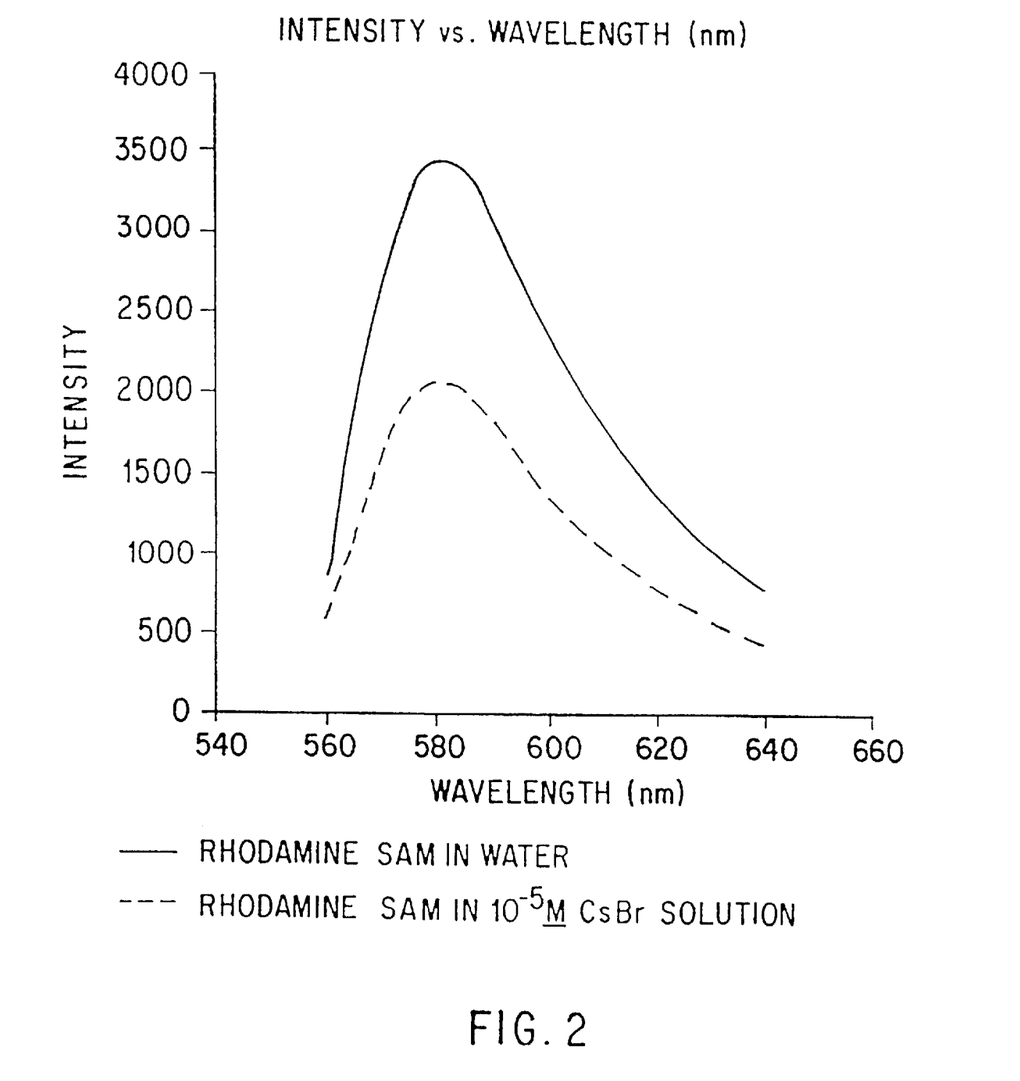
FIG. 2: Attenuation of fluorescence emission intensity of a rhodamine containing modular assembly formed upon analyte ($Cs^+$) binding.

Various receptors, including some based on native biomolecules (Sohanpal, K.; Watsuji, T.; Zhou, L. Q.; Cass, A. E. G., "Reagentless Fluorescence Sensors Based Upon Specific Binding Proteins," *Sensors & Actuators B* 11: 547, 1993) and some based on synthetic molecules (Fabbrizzi, L.; Licchelli, M.; Pallavicini, P.; Sacchi, D.; Taglietti, A. "Sensing of Transition Metals Through Fluorescence Quenching or enhancement: A Review," *Analyst* 121: 1763, 1996), exhibit changes in the conformation of their molecular chains upon binding of an analyte. On co-localization of these receptors with luminophors, electrophors (electron-transfer sensitive probes), or other reporters, in a modular assembly in the vicinity of a metal or other film that influences the emission properties of the reporter, the resulting change in receptor conformation results in a change; e.g., in the average distance between a luminophor reporter and the metal or other surface, and thus in a change in detectable luminescent properties of a luminophor. Any receptor change resulting from complex formation that influences the relative distance between the luminophor and the surface or otherwise affects its dielectric properties is utilizable for transduction according to the invention. FIG. 2 illustrates this transduction mechanism. In this illustration, a fluor covalently linked to the receptor is used to transduce a signal responsive to analyte binding.

IB. Change in Structure of the Assembly Near a Metallic or Other Influencing Surface.

Several other transduction mechanisms based on changes of assembly architecture are contemplated:

decrease in average separation of luminophors from a metallic or other surface (e.g., as a result of crosslinking or decrosslinking of the assembly upon analyte binding). Crosslinking and decrosslinking reactions can be induced by the presence of analyte through competitive dissociation. In this scheme, in the absence of analyte, the receptor is non-covalently bound to an analyte analog co-immobilized (e.g., covalently) in the molecular assembly. Upon exposure to analyte in solution, the receptor-analyte-analog couple is competitively dissociated owing to the formation of receptor-analyte complexes. In this embodiment, the receptor is labelled with a transducing probe [e.g., luminophor or redox probe (electrophor)], whose transduction properties are strongly influenced by the metallic or other support. Upon competitive dissociation via exposure to analyte (i.e., decrosslinking) the distance between the labeled receptor and the substrate changes (e.g., via diffusion). The sensor is made reversible by (1) linking the labeled receptor (e.g., covalently) through a flexible tether molecule (e.g., polyethylene glycol) to the support; or (2) by confining the receptor/analyte complex to the vicinity of the sensor surface by means of a selectively permeable membrane that does not allow transport of the larger receptor molecule (e.g., an antibody) but allows transport by the smaller analyte molecule.

increase in average separation of luminophors from a metallic or other surface (e.g., as a result of swelling of the modular assembly upon analyte binding). Swelling is usually caused by the excluded volume of the analyte, or by the removal of crosslinks by the analyte.

changes in average orientation of luminophors with respect to a metallic or other surface upon analyte binding.

Example II

Transduction Through Mediation of Transport of Quenchers.

Reagentless transduction can also be based on the use of quenchers capable of quenching excited states of a luminophor in the sample or sensing medium (e.g., $O_2$ in air or dissolved in water). In these assemblies, binding of the analyte to a receptor results in a change in the modular assembly which inhibits the transport of a molecular quencher (e.g., $O_2$) to the luminophor. Transport (e.g., diffusion) inhibition can be affected by, inter alia:

an occlusion of the surface of the assembly by the analyte (e.g., a protein);

a decrease in the porosity of the assembly, a change in the solid state diffusivity in the modular assembly.

Example III

Transduction in Modular Assemblies by Excimer Formation and Disruption, Resonance Energy Transfer, and Photoinduced Electron Transfer.

Figure 3A:
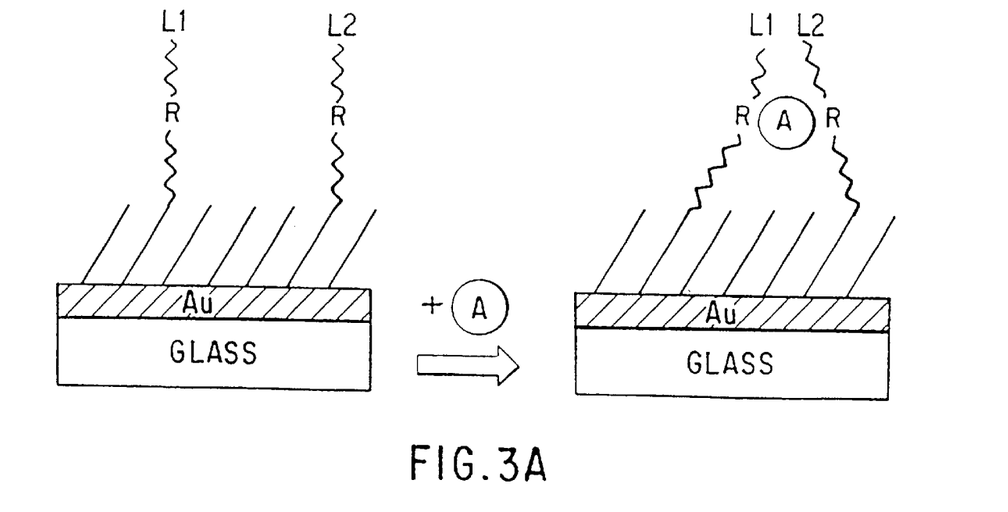
FIG. 3: Transduction in Modular Assemblies.
Figure 3B:
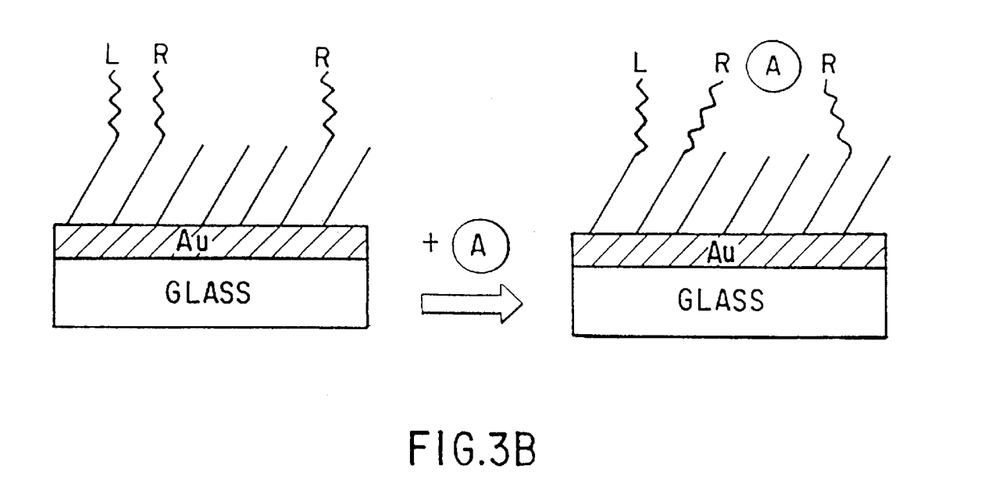
FIG. 3B: Binding of the analyte results in displacement of an effector module (R) away from the luminophore, increasing emission. R is, for example a quencher or is linked to a quencher.

Several reagentless transduction mechanisms based on the concept of modular design of responsive molecular assemblies are shown in FIG. 3.

Example IV

Transduction in Modular Assemblies by Analyte Quenching.

The modular incorporation of receptor and luminophor modules are disposed in close proximity in the assembly to cause a change in the photoemission characteristics of a luminescent reporter upon binding of the analyte to the receptor. Typical luminophor properties affected by the analyte include photoinduced charge transfer, resonance energy transfer, and changes in the local dielectric environment of the luminescent probe.

Example V

Figure 4A:
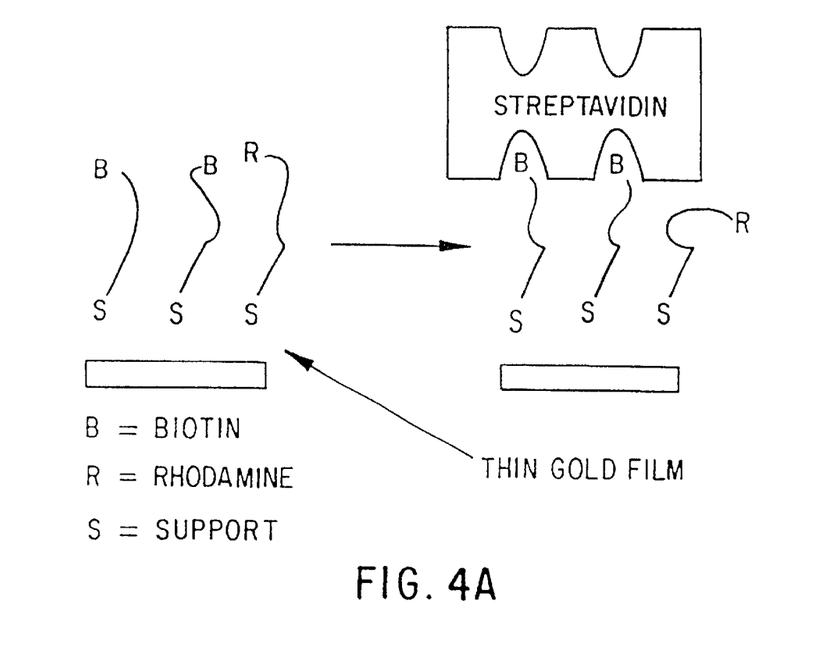
FIG. 4A illustrates in schematic form the reagentless transduction for specific binding of a model analyte (streptavidin) to a modular assembly on a metallic substrate (gold) in wbich biotin is the model receptor for stretavidin.
Figure 4B:
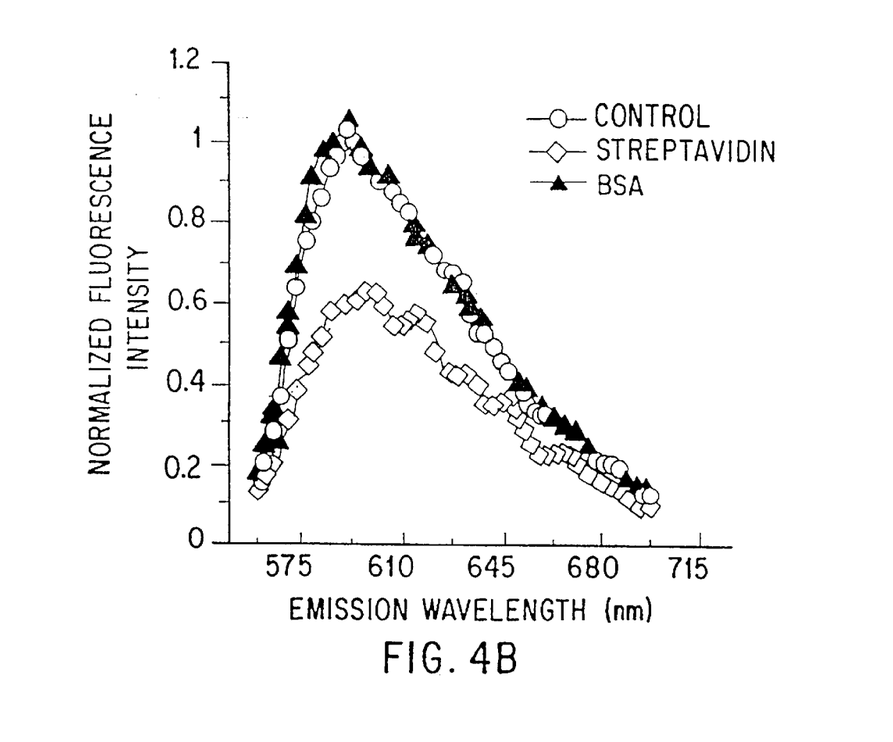
FIG. 4B is a graph of fluorescent spectrums of rhodamine in which open circles labeled "control" represent a fluorescence spectrum of reporter rhodamine from the assembly that has not been exposed to streptavidin, open diamonds labeled "streptavidin" represent a fluorescence spectrum of reporter rhodamine after exposure to streptavidin, and filled triangles labeled "BSA" represent a fluorescence spectrum of rhodamine after exposure to a receptor that does not bind to biotin
Figure 5A:
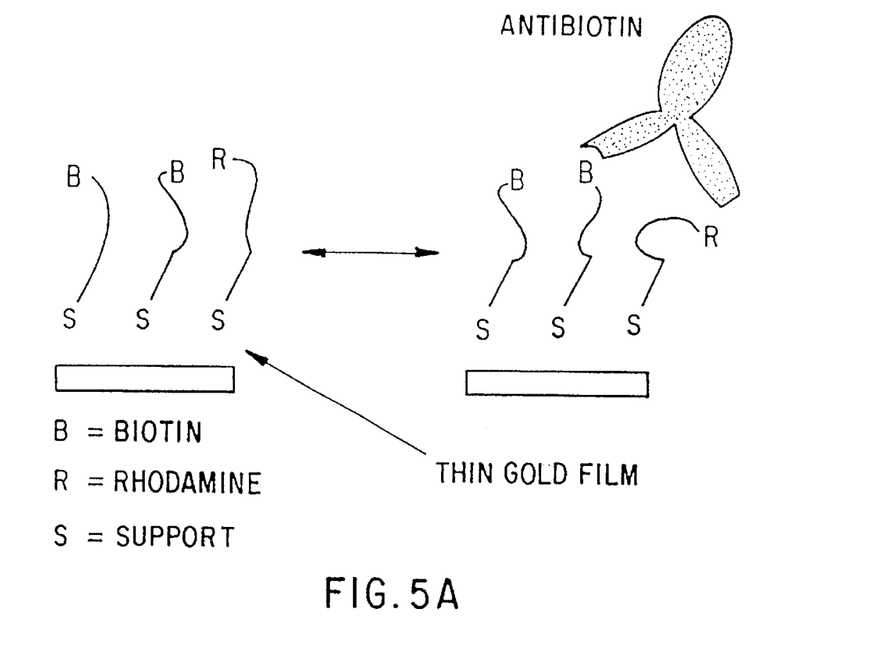
FIG. 5A illustrates in schematic form a reagentless transduction of reversible binding of a model analyte (antibiotin to a modular assembly on a metallic substrate (gold) in which biotin is the model receptor for antibiotin.
Figure 5B:
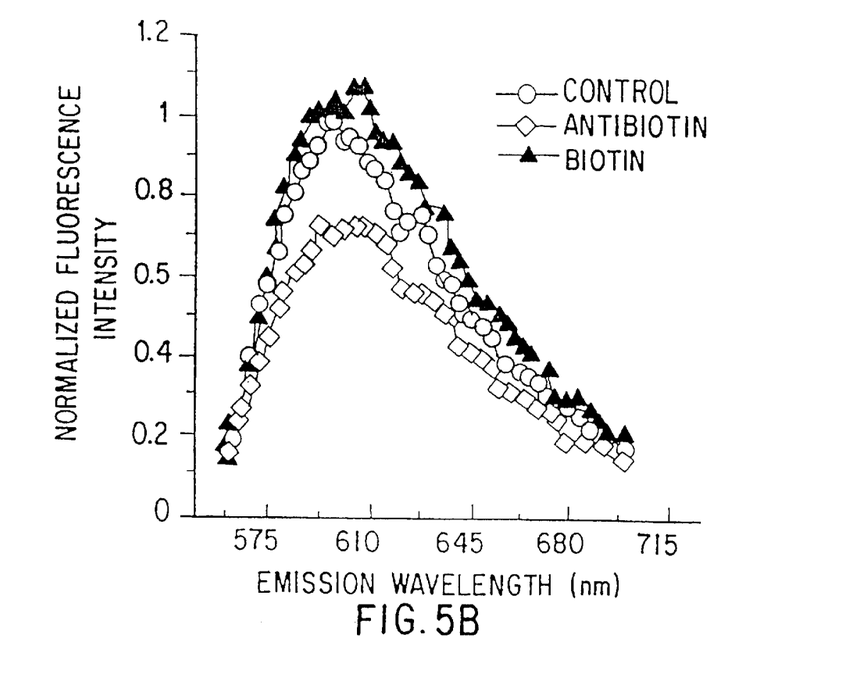
FIG. 5B is a graph of fluorescent spectrums for experiments based on the reagentless transduction of FIG. 5A in which open circles labeled "control" represent a fluorescence spectrum of reporter rhodamine from an assembly that has not been exposed to antibiotin, open diamonds labeled "antibiotin" represent a fluorescence spectrum of reporter rhodamine after exposure of antibiotin, and filled triangle labeled "biotin" represent a fluorescence spectrum of reporter rhodamine after elution of antibiotin from the assembly surface by exposure to excess biotin.

Examples are given in FIGS. 4 and 5 which schematically illustrate other specific and reversible reagentless transductions in the modular assemblies of the invention.

What is claimed is:

1. A modular assembly for affinity separation of an analyte from a sample comprising:

an affinity support comprised of a metal; and at least one sensor unit comprising:

an affinity module, said affinity module having a binding affinity for said analyte; and a signal-competent reporter module, said signal competent reporter module being directly or indirectly signal-responsive to complex formation between said affinity module and said analyte, wherein said signal competent reporter molecule is immobilized on said affinity support, and said signal-competent reporter module being spaced from said affinity support such that said complex formation provides a change in the distance between said signal-competent reporter module and said affinity support.

2. The modular assembly of claim 1, wherein the reporter module is indirectly responsive to complex formation and the modular assembly further includes an effector module associated with the affinity support for mediating reporter module signal response to complex formation.

3. The modular assembly of claim 1, wherein the reporter module comprises a luminophor.

4. The modular assembly of claim 2, wherein the reporter module comprises a luminophor.

5. The modular assembly of claim 3, wherein the signal response of the reporter module is directly induced by analyte binding.

6. The modular assembly of claim 5, wherein the signal response is induced by collisional quenching, photoinduced electron transfer, or resonance energy transfer.

7. The modular assembly of claim 4, wherein signal response of the reporter module is induced by displacement of this module relative to the effector module on complex formation.

8. The modular assembly of claim 7, wherein the signal response is induced by a change in the dielectric environment of the reporter module.

9. The modular assembly of claim 7, wherein the effector module comprises a metallic component.

10. The modular assembly of claim 1, wherein the affinity and reporter modules are immobilized on the support in spaced relationship.

11. An assay kit for detection of an analyte comprising the modular assembly of one of claims 1–10.

12. A method for detecting an analyte in a sample comprising exposing the modular assembly of one of claims 1–10 to the sample and detecting a signal from the reporter module.

13. The modular assembly of claim 1, wherein the reporter module comprises an electrophor.

14. The modular assembly of claim 2, wherein the reporter module comprises an electrophor.

15. The modular assembly of claim 3, wherein said change in the distance between said signal-competent reporter module and said support is measured from the luminescent center of said luminophor to said support.

16. The modular assembly of claim 4, wherein said change in the distance between said signal-competent reporter module and said support is measured from the luminescent center of said luminophor to said support.

17. The modular assembly of claim 13, wherein said electrophor is a redox reporter.

18. The modular assembly of claim 17, wherein said redox reporter is viologen.

19. The modular assembly of claim 14, wherein said electrophor is a redox reporter.

20. The modular assembly of claim 19, wherein said redox reporter is viologen.

21. The modular assembly of claim 13, wherein said electrophor is a redox enzyme.

22. The modular assembly of claim 21, wherein said redox enzyme is horseradish peroxidase.

23. The modular assembly of claim 14, wherein said electrophor is a redox enzyme.

24. The modular assembly of claim 23, wherein said redox enzyme is horseradish peroxidase.

25. The modular assembly of claim 1, wherein said affinity module is affixed to said support.

26. The modular assembly of claim 1, wherein said affinity module is affixed to said support and spaced apart from said signal-competent reporter module.

27. The modular assembly of claim 1, wherein said affinity module is affixed to said support and linked to said signal-competent reporter module.

28. The modular assembly of claim 1, wherein said signal-competent reporter module is spaced from said support such that fluorescence is not enched.

* * * * *